United States Patent [19]
Bacher et al.

[11] Patent Number: 6,045,586
[45] Date of Patent: Apr. 4, 2000

[54] COMPOUNDS HAVING ULTRA-VIOLET ABSORPTION PROPERTIES

[75] Inventors: Jean-Pierre Bacher, Buschwiller, France; Werner Kaufmann, Rheinfelden, Switzerland; Dieter Reinehr, Kandern, Germany

[73] Assignee: Ciba Specialty Chemicals Corporation, Tarrytown, N.Y.

[21] Appl. No.: 09/009,864

[22] Filed: Jan. 22, 1998

Related U.S. Application Data

[62] Division of application No. 08/471,816, Jun. 6, 1995, Pat. No. 5,741,905.

[30] Foreign Application Priority Data

Jul. 23, 1994 [GB] United Kingdom .................. 9414881
Sep. 1, 1994 [GB] United Kingdom .................. 9417562

[51] Int. Cl.⁷ ......................... D06M 13/00; C07D 251/38
[52] U.S. Cl. ..................... 8/115.59; 544/914; 544/206; 544/208; 544/215; 544/216
[58] Field of Search ........................ 68/115.59; 544/194, 544/206, 208, 215, 216

[56] References Cited

U.S. PATENT DOCUMENTS

| | | | |
|---|---|---|---|
| 4,895,945 | 1/1990 | Brown ..................................... | 544/218 |
| 5,189,084 | 2/1993 | Birbaum et al. ........................ | 524/100 |
| 5,420,204 | 5/1995 | Valet et al. .............................. | 525/125 |

FOREIGN PATENT DOCUMENTS

| | | |
|---|---|---|
| 165608 | 12/1985 | European Pat. Off. . |
| 388356 | 9/1990 | European Pat. Off. . |
| 0434608 | 6/1991 | European Pat. Off. . |
| 0538839 | 4/1993 | European Pat. Off. . |
| 9404515 | 3/1994 | WIPO . |

OTHER PUBLICATIONS

Chem. Abst. 110:39941X, 1989.
Chem. Abst. 97:144884, 1982.
Chem. Abst. 109:75134, 1988.
Chem. Abst. 96:53842, 1981.
Chem. Abst. 98:188980, 1983.

*Primary Examiner*—Yogendra N. Gupta
*Attorney, Agent, or Firm*—Kevin T. Mansfield

[57] ABSTRACT

The present invention relates to new compounds which are useful as ultraviolet absorbing agents (UVAs) and to a method of improving the sun protection factor (SPF) of textile fibre material treated with the new compounds.

23 Claims, No Drawings

COMPOUNDS HAVING ULTRA-VIOLET ABSORPTION PROPERTIES

This application is a divisional of prior application Ser. No. 08/471,816 filed Jun. 6, 1995, U.S. Pat. No. 5,741,905.

The present invention relates to new compounds which are useful as ultraviolet absorbing agents (UVAs) and to a method of improving the sun protection factor (SPF) of textile fibre material treated with the new compounds.

It is known that light radiation of wavelengths 280–400 nm permits tanning of the epidermis. Also known is that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, even skin beneath clothing dyed in some dark shades may also require protection from UV radiation.

Such lightweight summer clothing normally has a density of of less than 200 g/m² and has a sun protection factor rating between 1.5 and 20, depending on the type of fibre from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, SPF ratings of at least 20 are desired for lightweight clothing.

It is already known, e.g. from WO 94/4515, that the application of specified types of UVA to a light-weight textile materials in general can effect an increase in the SPF value of the textile so treated. The increase in SPF value achieved thereby, however, is relatively modest.

Certain new compounds have now been found which can be readily produced and which, unexpectedly, impart greatly increased SPF ratings to textile fibre materials treated with the new compounds.

Accordingly, the present invention provides a compound having the formula:

(1)

in which m is 1 or 2: A is a residue selected from those having the formulae:

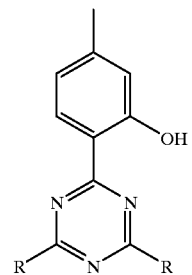

(2)

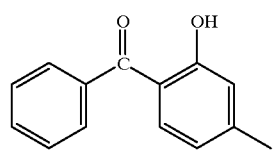

(3)

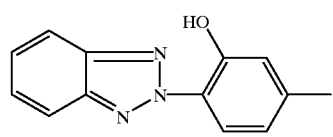

(4)

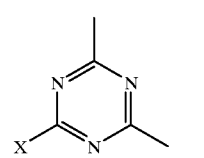

(5)

or

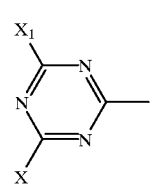

(6)

in which R is phenyl, optionally substituted by 1 or 2 $C_1$–$C_4$ alkyl groups, preferably tolyl or xylyl, or by 1 or 2 $C_1$–$C_{18}$ alkoxy groups, or R is a group having the formula:

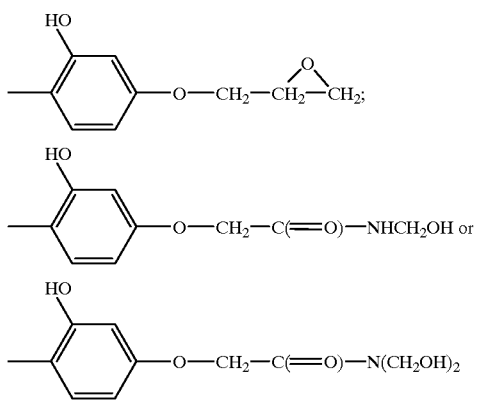

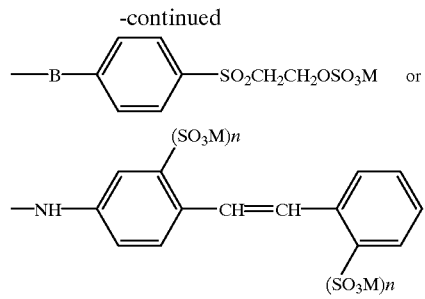

in which B and M have their previous significance and n is 0 or 1, provided that at least one $SO_3M$ group is present, or the formula:

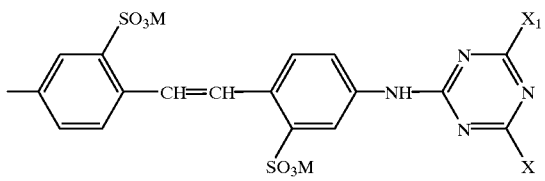

in which X, $X_1$ and M have their previous significance; provided that the following compounds are excluded:

a) those in which A is a residue of formula (2), (3) or (4), B is —O— and D is a group of formula

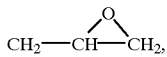

$CH_2$—$C(=O)$—$NH(CH_2OH)$ or $CH_2$—$C(=O)$—$N(CH_2OH)_2$;

b) the compound 4-glycidyloxy-2-hydroxy benzophenone; and c) the compound 2-(2-hydroxy-4-glycidyloxy)-4,6-(2,4-dimethylpheny)-1,3,5-triazine.

Preferred compounds of formula (1) include those having one of the formulae:

(7)

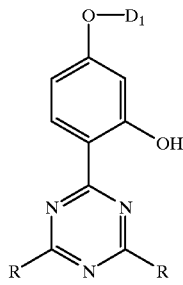

in which R has its previous significance and $D_1$ is a group having the formula

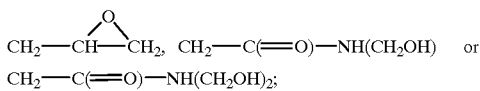

X is F, Cl or $NHCH_2OH$ and $X_1$ is F, Cl, $NHCH_2OH$ or a group having the formula:

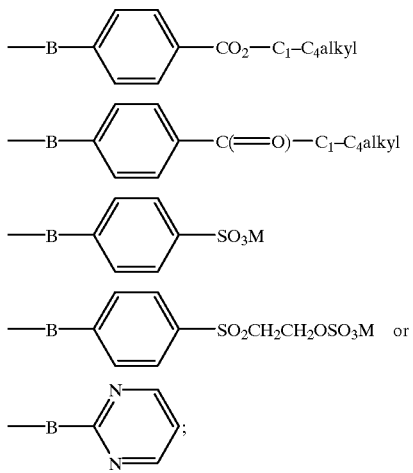

B is —O—, —NH— or —$SO_2$—; and
D is a group having one of the formulae:

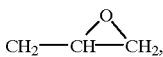

$CH_2$—$C(=O)$—$NH(CH_2OH)$, $CH_2$—$C(=O)$—$N(CH_2OH)_2$ or —$CH_2CH_2$—$OSO_3M$ in which M is hydrogen, sodium, potassium, calcium, magnesium, ammonium, mono-, di-, tri- or tetra-$C_1$-$C_4$ alkylammonium or ammonium that is di- or tri-substituted by a mixture of $C_1$-$C_4$ alkyl and $C_1$-$C_4$ hydroxyalkyl groups, preferably sodium, or, when A is a residue of formula (5) or (6), D may also be a group of formula:

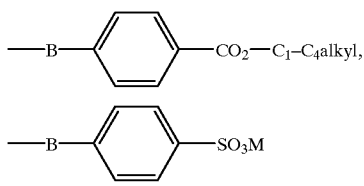

(8)

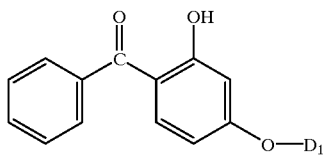

in which D₁ has its previous significance;

(9)

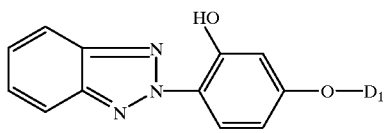

in which D₁ has its previous significance;

(10)

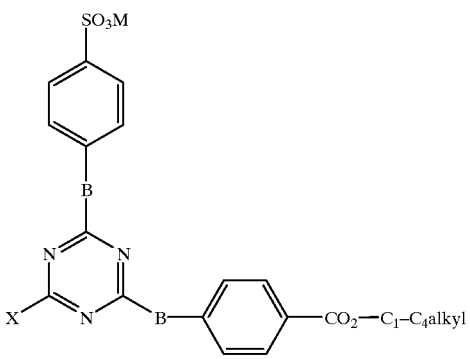

or (11)

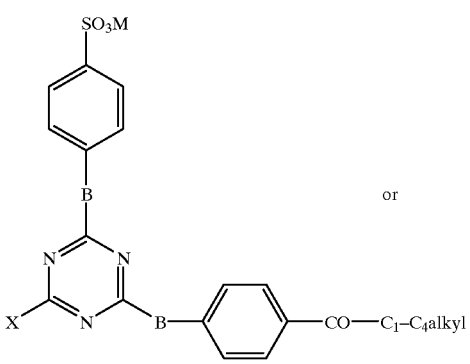

(12)

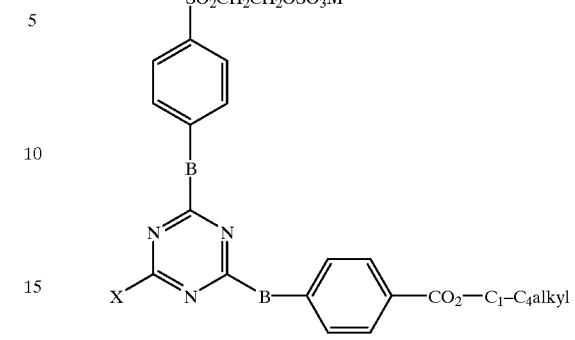

in which X is F or Cl and B and M have their previous significance and in which preferably X is Cl, B is NH and M is Na;

(13)

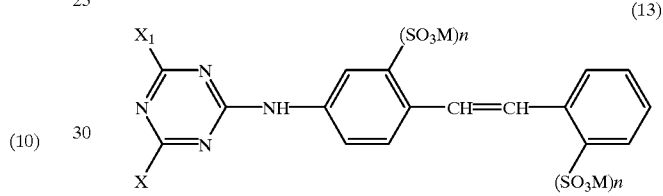

in which n has its previous significance, provided that at least one group —SO₃M is present, X is F or Cl and X₁ is F, Cl or a group having one of the formulae:

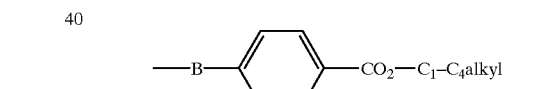

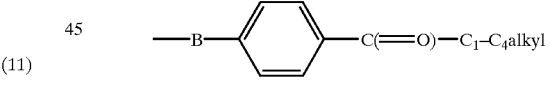

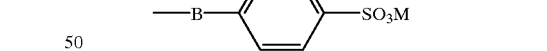

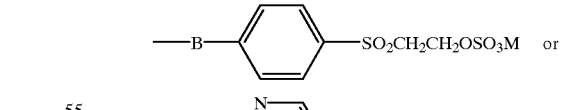 or

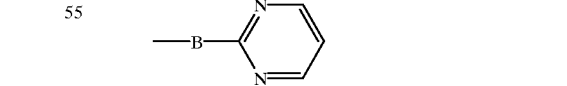

in which B and M have their previous significance;

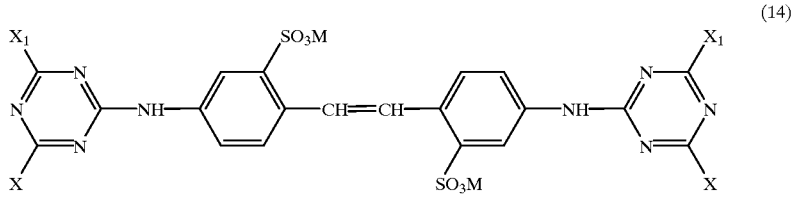

(14)

in which each X is the same and is F or Cl and each $X_1$ is the same and is F, Cl or a group having one of the formulae:

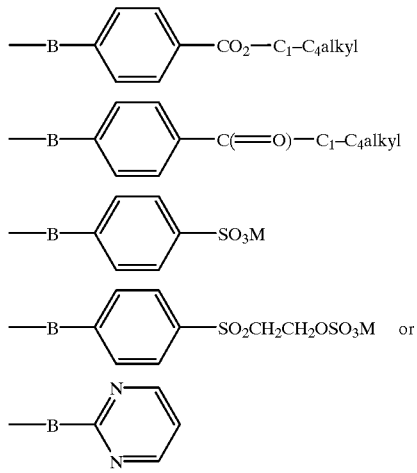

in which B and M have their previous significance, or

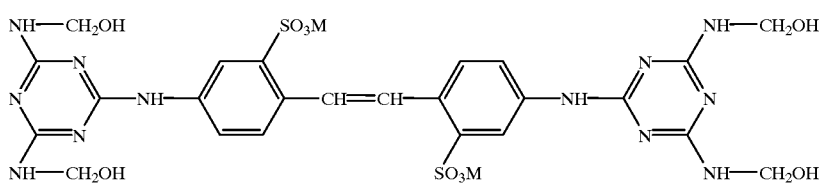

(15)

in which M has its previous significance but is preferably Na.

The compounds of formula (1) may be produced by reacting, under known reaction conditions, a compound of formula $A\text{-}(BH)_m$ in which A, B and m have their previous significance, with m moles of a compound L-D, in which D has its previous significance and L is a leaving group or atom, preferably a halogen atom, especially a chlorine atom The starting materials $A\text{-}(BH)_m$ and L-D are known compounds which are readily available.

The present invention also provides a method for the treatment of a textile fibre material, comprising treating the textile fibre material with 0.05 to 3.0% by weight, based on the weight of the textile fibre material, of one or more compounds having the formula (1).

The textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres.

Preferably, textile fibres treated according to the method of the present invention have a density of less than 200 g/m² and have not been previously dyed in deep shades.

Some of the compounds of formula (1) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1) there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$–$C_6$ alkanols, the addition products having been converted into an acid ester with an organic dicarboxylic acid or with an inorganic polybasic acid;

lignin sulphonates; and, in particular formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1), or its emulsions in organic solvents may also be used in the method of the present invention. For example, the so-called solvent dyeing (pad thermofix application) or exhaust dyeing methods in dyeing machines may be used If the method of the present invention is combined with a textile treatment or finishing method, such combined treatment may be advantageously carried out using appropriate stable preparations which contain the compound of formula (1) in a concentration such that the desired SPF improvement is achieved.

In certain cases, the compound of formula (1) is made fully effective by an after-treatment. This may comprise a chemical treatment such as treatment with an acid, a thermal treatment or a combined thermal/chemical treatment.

It is often advantageous to use the compound of formula (1) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1), a minor proportion of one or more adjuvants may also be employed in the method of the present invention. Examples of adjuvants include emulsifiers, perfumes, colouring dyes, opacifiers, optical whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1% by weight on the treated fibre.

The method of the present invention, in addition to providing protection to the skin, also increases the useful life of a textile article treated according to the present invention. In particular, the tear resistance and/or lightfastness of the treated textile fibre material may be improved.

Accordingly, the present invention still further provides a method of increasing the SPF rating of textile fibre material, comprising treating the textile fibre material with 0.05 to 3.0% by weight, based on the weight of the textile fibre material, of one or more compounds having the formula (1).

The present invention also provides a textile fabric produced from a fibre treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The following Examples further illustrate the present invention.

EXAMPLE 1

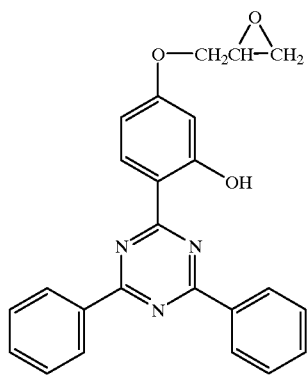

(101)

13.1 g. of 2-(2,4-dihydroxyphenyl)-4,6-diphenyl-1,3,5-triazine are stirred with 7.3 g. of potassium carbonate and 100 ml. of epichlorhydrin over 5 hours at 110° C. After cooling the reaction mixture to 25° C. and diluting it with 150 mls. of ethanol, the product which is thereby precipitated is filtered off, washed and dried in vacuum at 80° C. The compound (101) having the above structure is obtained in a yield corresponding to 88.1% of the theoretical yield and has the following elemental analysis by weight:

Analysis for $C_{27}H_{19}N_3O_3$: Req. % C, 72.53; H, 4.82; N, 10.57 Found % C, 72.3; H, 4.9; N, 10.4.

EXAMPLE 2

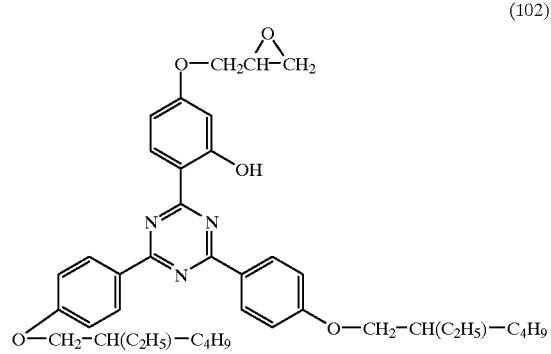

(102)

Using the procedure described in Example 1, but employing 2-(2,4-dihydroxyphenyl)-4,6-di(4'-2'-ethylhexoxy) phenyl-1,3,5-triazine instead of 2-(2,4-dihydroxyphenyl)-4,6-diphenyl-1,3,5-triazine, compound (102) is obtained in a yield of 86.3% of the theoretical and has the following elemental analysis by weight:

Analysis for $C_{40}H_{51}N_3O_5$: Req. % C, 73.78; H, 7.86; N, 6.43 Found % C, 73.3; H, 8.05; N, 6.13.

EXAMPLE 3

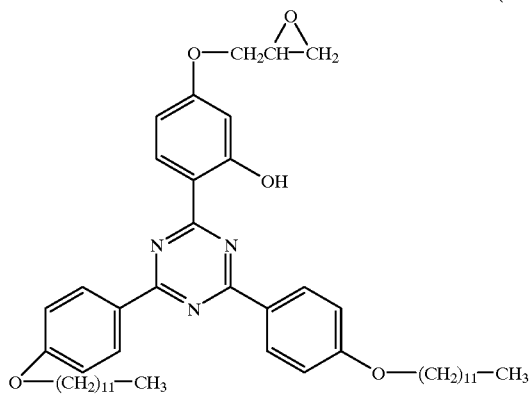
(103)

Using the procedure described in Example 1, but employing 2-(2,4-dihydroxyphenyl).-4,6-di(4'-dodecoxy)phenyl-1,3,5-triazine instead of 2-(2,4-dihydroxyphenyl) 4,6-diphenyl-1,3,5-triazine, compound (103) is obtained in a yield of 86.3% of the theoretical and has the following elemental analysis by weight:

Analysis for $C_{48}H_{67}N_3O_5$: Req. % C, 75.26; H, 8.82; N, 5.49 Found % C, 75.1; H, 8.8; N, 5.5.

EXAMPLE 4

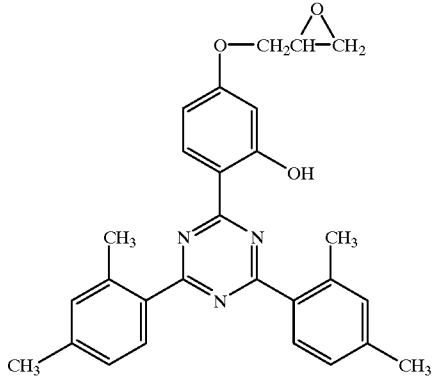
(104)

Using the procedure described in Example 1, but employing 2-(2,4-dihydroxyphenyl)-4,6-dixylyl-1,3,5-triazine instead of 2-(2,4-dihydroxyphenyl)-4,6-diphenyl-1,3,5-triazine, compound (104) is obtained in a yield of 85% of the theoretical and has the following elemental analysis by weight:

Analysis for $C_{28}H_{27}N_3O_3$: Req. % C, 74.15; H, 6.00 N, 9.26 Found % C, 74.3; H, 6.2; N, 9.3.

Compound (104) is known having been described in Example 6 of EP 526 399.

EXAMPLE 5

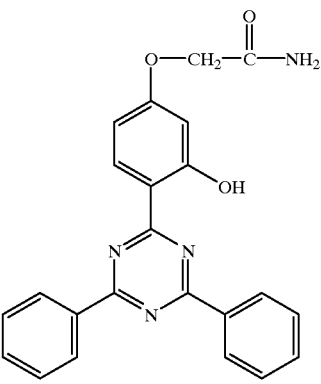
(105a)

A) A mixture of 28.5 g. 2-(2,4-dihydroxyphenyl)-4,6-diphenyl-1,3,5-triazine, 9.4 g. potassium hydroxide, 31.2 g. chloracetamide and 650 mls. ethanol is stirred at 70° C. for 16 hours. After cooling, the precipitate is filtered off, washed with water and recrystallised twice from methylcellosolve.

17.5 g. of a light beige product (105a) are obtained in a yield corresponding to 52.5% of the theoretical yield. The product has the following elemental analysis by weight:

Analysis for $C_{23}H_{18}N_4O_3$: Req. % C, 67.73; H, 4.66; N, 13.74 Found % C, 67.9; H, 4.7; N, 13.6.

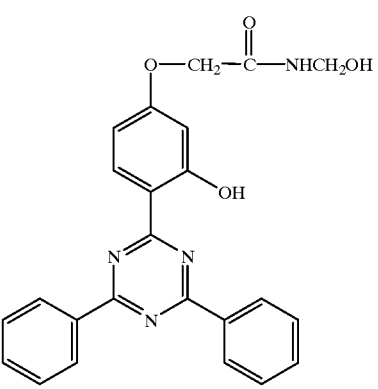
(105b)

B) 8 g. of the compound (105a) are stirred in 250 mls. of dimethylacetamide and the mixture is rendered alkaline by the addition of 5 drops of 30% caustic soda solution. After the addition of 20 mls. of a 36% formalin solution, the reaction mixture is heated to 70° C. and stirred for 4 hours at this temperature. The reaction solution is poured into 1.5 liters of water and the resulting solid product is filtered off. After recrystallisadon from dioxan, there are obtained 4.8 g. of a light yellow product, corresponding to a yield of 56% of the theoretical. The product (105b) has the following elemental analysis by weight:

Analysis for $C_{27}H_{20}N_4O_4 \cdot 0.33\ H_2O$: Req. % C, 66.30; H, 4.75; N, 12.89 Found % C, 66.3; H, 4.9; N, 12.7.

EXAMPLE 6

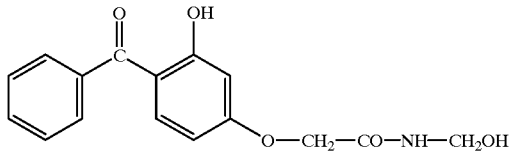
(106)

Using the procedure described in Example 5, but employing 2,4-dihydroxybenzophenone instead of 2-(2,4-dihydroxyphenyl)-4,6-diphenyl-1,3,5-triazine, compound (106) is obtained in a yield of 56% of the theoretical and has the following elemental analysis by weight:

Analysis for $C_{16}H_{15}NO_5$. 0.55 $H_2O$: Req. % C, 58.4; H, 4.9; N, 4.26; $H_2O$ 2.99 Found % C, 58.4; H, 5.5; N, 4.1; $H_2O$ 2.99.

EXAMPLE 7

(107)

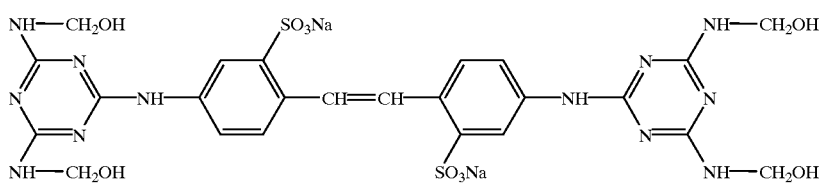

6.3 g. of the compound of formula:

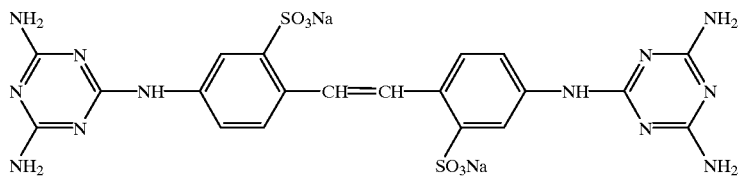

are dissolved in 150 mls. of water at 60° C. and treated with 10 drops of 30% caustic soda solution. After the dropwise addition of 32.4 g. of a 37% formaldehyde solution, and subsequent stirring at 60–65° C. over 2.5 hours, 150 mls. of salt solution are added and the mixture is cooled to 10° C. The reaction mixture is filtered giving 7 g. of a solid product, corresponding to a yield of 93% of the theoretical.

The product (107) has the following elemental analysis by weight:

Analysis for $C_{27}H_{26}N_{12}Na_2O_{10}S_2$. 1 $C_2H_5OH$. 7.5$H_2O$: Req. % C, 33.47; H, 4.93; N, 18.00; S, 6.87; Na, 4.93 Found % C, 33.4; H, 4.7; N, 17.5; S, 6.7; Na, 5.0.

EXAMPLE 8

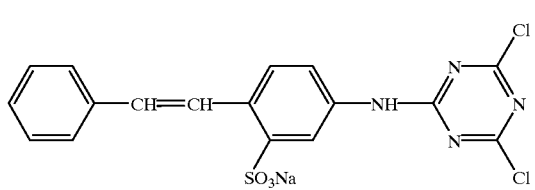
(108)

3.4 g. of cyanuric chloride are stirred in a mixture of 100 mls of acetone and 50 mls of water. The mixture is chilled to −10° C. and a solution of 5.5 g. of 4-aminostilbene-2-sulfonic acid sodium salt in 50 mls of water is added over 30 minutes, followed by 10 mls of II sodium carbonate solution.

The resulting mixture is stirrd for 2 hours at −5 to −10° C. and the solid is filtered off and dried, giving 6.8 g. of a white product corresponding to a yield of 74% of theory.

The compound (108) has the following elemental analysis by weight:

Analysis for $C_{17}H_{11}Cl_2N_4NaO_3S$. 1.26 $H_2O$: Req. % C, 43.63; H, 2.91; N, 11.97; S, 6.85; Cl, 15.15; $H_2O$ 4.85 Found % C, 43.7; H, 3.0; N, 12.0; S, 6.8; Cl, 15.0.; $H_2O$ 4.85.

EXAMPLE 9

(109)

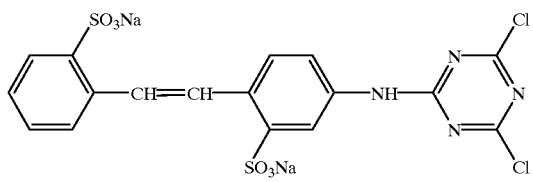

Using the same procedure as in Example 8 but replacing 4-aminostilbene-2-sulfonic acid by 4-aminostilbene-2,2'-disulfonic acid disodium salt, 15.1 g. of the compound of formula (109) are obtained, corresponding to a yield of 55% of theory.

The compound (109) has the following elemental analysis by weight:

Analysis for $C_{17}H_{10}Cl_2N_4Na_2O_6S_2$. 4.63 $H_2O$: Req. % C, 32.37; H, 3.03; N, 8.88; S, 10.17; Cl, 11.24; $H_2O$ 13.22 Found % C, 32.4; H, 3.0; N, 8.9; S, 10.0; Cl, 11.5.; $H_2O$ 13.23.

EXAMPLE 10

A) Using the procedure described in Example 8, prior to the filtration step, Compound (108) is produced as a white dispersion.

B) To this dispersion there are added 3 g. of 4-amino-ethylbenzoate, as a solid, followed by 10 mls of 1M sodium carbonate solution. The resulting pale yellow suspension is stirred for 18 hours at 25° C. and the solid product is filtered off and dried, giving 8.6 g. of the white compound of formula (110), corresponding to a yield of 83% of theory.

The compound (110) has the following elemental analysis by weight:

Analysis for $C_{26}H_{21}ClN_5NaO_5S$. 3.84 $H_2O$. 0.14 NaCl: Req. % C, 47.9; H, 4.4; N, 10.75; S, 4.9; Cl, 6.21; $H_2O$ 10.61 Found % C, 47.9; H, 4.4; N, 10.8; S, 4.8; Cl, 6.5.; $H_2O$ 10.76.

A) Using the procedure described in Example 8, prior to the filtration step, Compound (108) is produced as a white dispersion.

B) The procedure described in part B) of Example 10 is repeated except that 4-amino-ethylbenzoate is replaced by 4-amino-acetophenone. In this way, 4.8 g. of the white compound of formula (111) are produced, corresponding to a yield of 49% of theory.

The compound (111) has the following elemental analysis by weight:

Analysis for $C_{25}H_{19}ClN_5NaO_4S$. 3.96 $H_2O$. 0.16 NaCl: Req. % C, 48.0; H, 4.31; N, 11.2; S, 5.12; Cl, 6.59; $H_2O$ 11.40 Found % C, 48.0; H, 4.4; N, 11.3; S, 5.1; Cl, 6.4.; $H_2O$ 11.42.

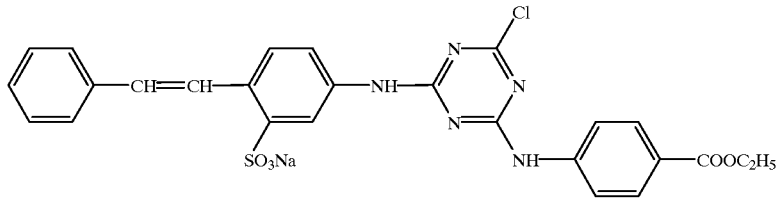

(110)

EXAMPLE 11

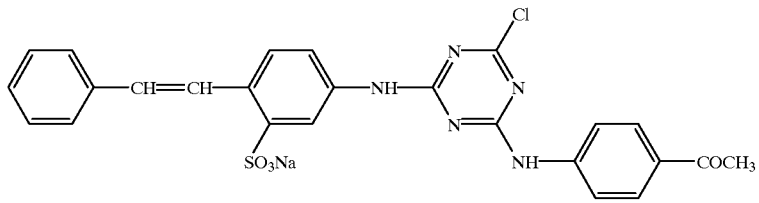

(111)

EXAMPLE 12

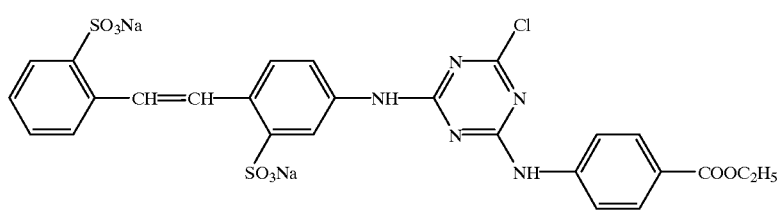
(112)

A) Using the procedure described in Example 9, prior to the filtration step, Compound (109) is produced as a dispersion.

B) The procedure in part B) of Example 10 is used for the reaction of the compound of formula (109) with 4-amino-ethylbenzoate to obtain 31.9 g. of the yellow compound (112), corresponding to a yield of 78.6% of theory.

The compound (112) has the following elemental analysis by weight:

Analysis for $C_{26}H_{20}ClN_5Na_2O_8S_2$. 6 $H_2O$. 0.5 NaCl: Req. % C, 38.4; H, 3.94; N, 8.6; S, 7.8; Cl, 6.5; $H_2O$ 13.28 Found % C, 38.9; H, 3.9; N, 9.2; S, 7.7; Cl, 6.6.; $H_2O$ 12.67.

EXAMPLE 13

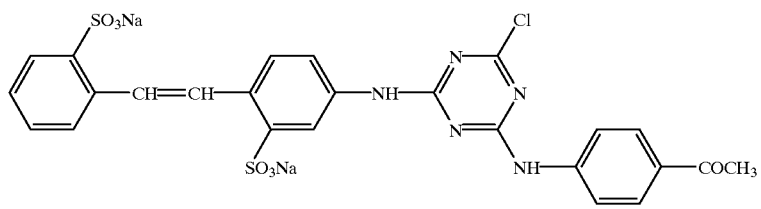
(113)

The procedure in Example 12 is repeated except that, in part B), 4-amino-acetophenone is used instead of 4-amino-ethylbenzoate. In this way, 6.3 g. of compound (113) are obtained, corresponding to a yield of 49% of theory.

The compound (113) has the following elemental analysis by weight:

Analysis for $C_{25}H_{18}ClN_5Na_2O_7S_2$. 4.61 $H_2O$.: Req. % C, 41.19; H, 3.76; N, 9.61; S, 8.80; Cl, 4.86; $H_2O$ 11.39 Found % C, 41.4; H, 3.8; N, 9.7; S, 8.6; Cl, 5.3.; $H_2O$ 11.39.

EXAMPLE 14

The procedure in Example 12 is repeated except that, in part B), 2-amino-pyrimidine is used instead of 4 amino-ethylbenzoate. In this way, 9.2 g. of compound (114) are obtained, corresponding to a yield of 61% of theory.

The compound (114) has the following elemental analysis by weight:

Analysis for $C_{21}H_{14}ClN_7Na_2O_6S_2$. 6 $H_2O$. 0.33 NaCl: Req. % C, 34.37; H, 3.55; N, 13.37; S, 8.7; Cl, 6.4; $H_2O$ 14.7 Found % C, 34.4; H, 3.6; N, 13.9; S, 8.5; Cl, 6.3.; $H_2O$ 15.1.

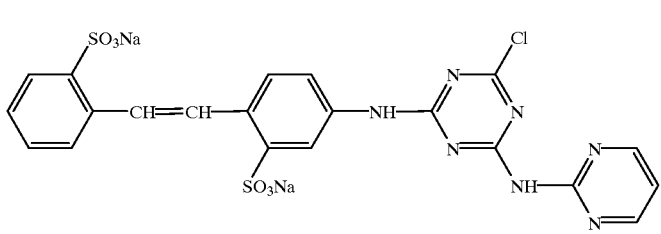
(114)

EXAMPLE 15

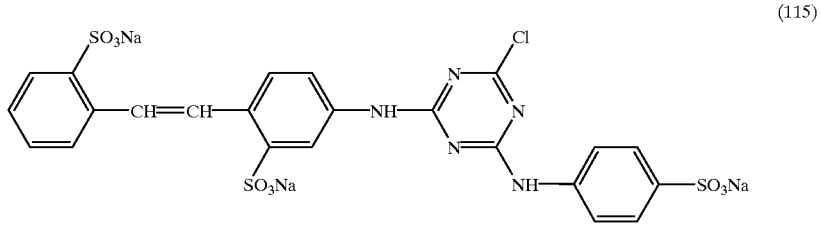
(115)

The procedure in Example 12 is repeated except that, in part B), sulfanilic acid is used instead of 4-amino-ethylbenzoate. In this way, 16.9 g. of compound (115) are obtained, corresponding to a yield of 57.9% of theory.

The compound (115) has the following elemental analysis by weight:

Analysis for $C_{25}H_{15}ClN_5Na_3O_9S_3$. 10.67 $H_2O$. 3.5 NaCl: Req. % C, 25.7; H, 3.11; N, 6.0; S, 8.22; Cl, 13.7; $H_2O$ 16.45 Found % C, 25.7; H, 3.2; N, 6.5; S, 8.5; Cl, 13.7.; $H_2O$ 16.4.

EXAMPLE 16

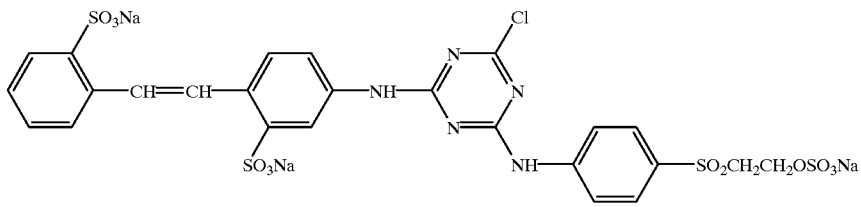
(116)

The procedure in Example 12 is repeated except that, in part B), 2-(4-aminophenylsulfonyl)-ethylhydrogen sulfate is used instead of 4-amino-ethylbenzoate. In this way, 19.5 g. of compound (116) are obtained, corresponding to a yield of 60% of theory.

The compound (116) has the following elemental analysis by weight:

Analysis for $C_{25}H_{21}ClN_5Na_3O_{12}S_4$. 8 $H_2O$. 0.41 $Na_2SO_4$: Req. % C, 29.50; H, 3.63; N, 6.88; S, 13.86; Cl, 3.49; $H_2O$ 14.15 Found % C, 29.5; H, 3.50; N, 7.0; S, 13.7; Cl, 3.7.; $H_2O$ 14.38.

EXAMPLE 17

Using the procedure described in Example 8, 18.4 g. of cyanuric chloride are stirred in a mixture of 120 mls of acetone and 100 mls of water. The mixture is chilled to −10° C. and a solution of 25.4 g. of 4.4'-diaminostilbene-2,2'-disulfonic acid disodium salt in 50 mls of water is added over 30 minutes, followed by 50 mls of IM sodium carbonate solution.

The resulting mixture is stirred for 2 hours at −5 to −10° C. and the solid is filtered off and dried, giving 24.1 g. of a. white product corresponding to a yield of 67.9% of theory.

The compound (117) has the following elemental analysis by weight:

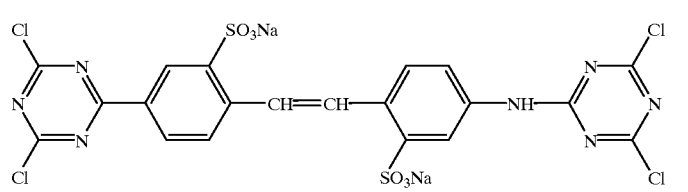
(117)

Analysis for $C_{20}H_{10}Cl_4N_8Na_2O_6S_2 \cdot 5\ H_2O$: Req. % C, 30.01; H, 2.51; N, 14.00; S, 8.01; Cl, 17.62; Found % C, 30.0; H, 2.6; N, 14.0; S, 7.8; Cl, 17.6.

EXAMPLE 18

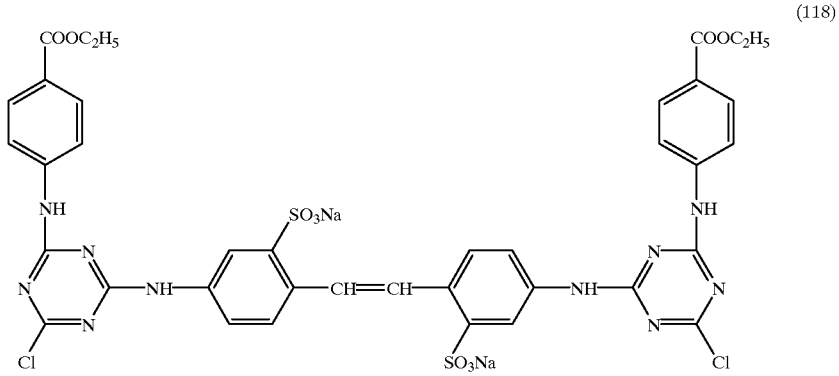

(118)

To the white suspension of the compound of formula (117) obtained in Example 17, prior to the filtration step, there is added 4-amino-ethylbenzoate in the manner described in Example 10.

In this way, 44.5 g. of compound (118) are obtained, corresponding to a yield of 92% of theory.

The compound (118) has the following elemental analysis by weight:

Analysis for $C_{38}H_{30}Cl_2N_{10}Na_2O_{10}S_2 \cdot 6.5\ H_2O \cdot 1\ NaCl$: Req. % C, 40.0; H, 3.77; N, 12.28; Cl, 9.34; $H_2O$ 10.26 Found % C, 40.0; H, 3.8; N, 12.3; Cl, 9.2.; $H_2O$ 10.0.

EXAMPLE 19

Using the procedure described in Example 18 but replacing 4-amino-ethylbenzoate by 4-amino-acetophenone, 29.1 g. of compound (119) are obtained, corresponding to a yield of 94.6% of theory.

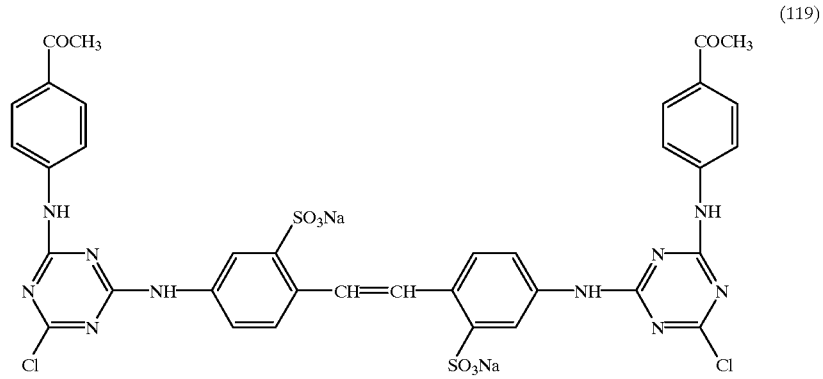

(119)

The compound (119) has the following elemental analysis by weight:

Analysis for $C_{36}H_{26}Cl_2N_{10}Na_2O_8S_2$. 16 $H_2O$. 0.6 NaCl: Req. % C, 35.15; H, 4.71; N, 11.38; Cl, 7.50; S, 5.20; $H_2O$ 10.26 Found % C, 35.1; H, 4.8; N, 11.5; Cl, 7.7.; S, 5.2; $H_2O$ 23.5.

EXAMPLE 20

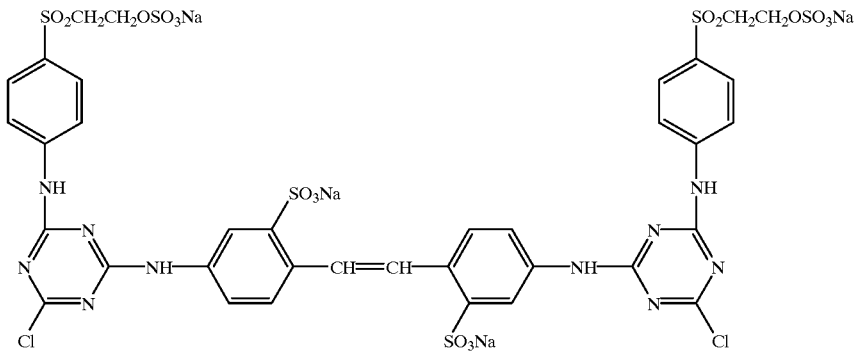

(120)

Using the procedure described in Example 18 but replacing 4-amino-ethylbenzoate by 2(4-aminophenylsulfonyl)-ethylhydrogensulfate, 46.2 g. of compound (120) are obtained, corresponding to a yield of 73. 1% of theory.

The compound (120) has the following elemental analysis by weight:

Analysis for $C_{36}H_{30}Cl_2N_{10}Na_4O_{18}S_6$. 12.05 $H_2O$. 18.2 NaCl: Req. % C, 17.10; H, 2.14; N, 5.53; S, 7.59; Cl, 28.33; $H_2O$ 8.58 Found % C, 17.1; H, 2.1; N, 5.6; S, 7.5; Cl, 28.6; $H_2O$ 8.58.

EXAMPLE 21

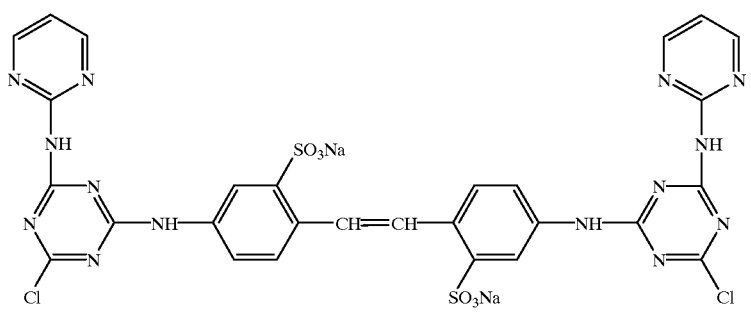

(121)

Using the procedure described in Example 18 but replacing 4-amino-ethylbenzoate by 4-aminopyrimidine, 16.4 g. of compound (121) are obtained, corresponding to a yield of 79% of theory.

The compound (121) has the following elemental analysis by weight:

Analysis for $C_{26}H_{18}Cl_2N_{14}Na_2O_6S_2$. 7.3 $H_2O$. 0.7 NaCl. 1 $CH_3COCH_3$: Req. % C, 33.42; H, 3.75; N, 18.85; Cl, 9.20; S, 6.15 Found % C, 33.3; H, 3.5; N, 19.0; Cl, 9.3; S, 6.1.

EXAMPLE 22

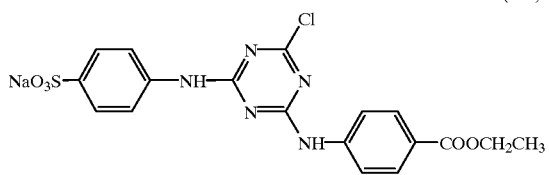

(122)

Using the procedure described in Example 8 but replacing 4-amino-stilbene-2-sulfonic acid sodium salt by a mixture of sulfanilic acid and 4-aminoethylbenzoate, in the required stoichiometric proportions, 41 g. of the compound of formula (122) are obtained, corresponding to a yield of 87% of theory.

The compound (122) has the following elemental analysis by weight:

Analysis for $C_{18}H_{15}ClN_5NaO_5S$. 3.67 $H_2O$: Req. % C, 40.19; H, 4.19; N, 13.02; Cl, 6.59; S, 5.96; $H_2O$ 12.29 Found % C, 40.4; H, 4.2; N, 13.1; Cl, 6.59; S, 6.1; $H_2O$ 12.3.

EXAMPLE 23

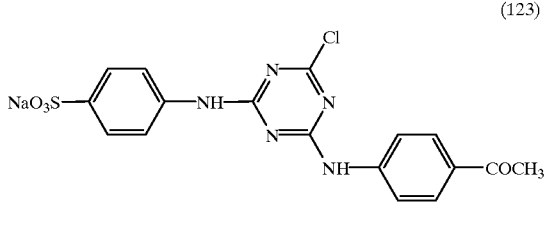

(123)

Using the procedure described in Example 8 but replacing 4 amino-stilbene-2-sulfonic acid sodium salt by a mixture of sulfanilic acid and 4-aminoacetophenone, in the required stoichiometric proportions, 20.1 g. of the compound of formula (123) are obtained, corresponding to a yield of 91% of theory.

The compound (123) has the following elemental analysis by weight:

Analysis for $C_{17}H_{13}ClN_5NaO_4S$. 4 $H_2O$. 0.25 NaCl: Req. % C, 38.64; H, 3.97; N, 13.24; Cl, 8.38; S, 6.06; $H_2O$ 13.62 Found % C, 39.1; H, 4.0; N, 13.5; Cl, 8.6; S, 6.0; $H_2O$ 13.31.

EXAMPLE 24

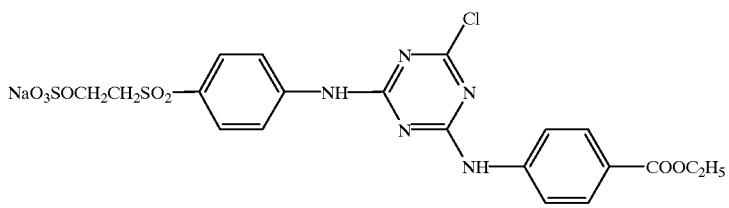

(124)

Using the procedure described in Example 8 but replacing 4-amino-stilbene-2-sulfonic acid sodium salt by a mixture of 2-(4-aminophenylsulfonyl)ethylhydrogen sulfate and 4-amino-ethylbenzoate, in the required stoichiometric proportions, 9.3 g. of the compound of formula (124) are obtained, corresponding to a yield of 73% of theory.

The compound (124) has the following elemental analysis by weight:

Analysis for $C_{20}H_{19}ClN_5NaO_8S_2$. 3.5 $H_2O$. 4.5 NaCl: Req. % C, 25.40; H, 2.75; N, 7.41; S, 6.77; $H_2O$ 6.60 Found % C, 25.4; H, 2.6; N, 7.4; S, 6.2; $H_2O$ 6.5.

EXAMPLE 25

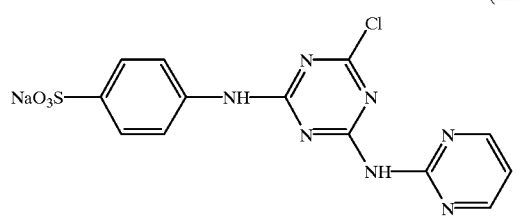

(125)

Using the procedure described in Example 8 but replacing 4-amino-stilbene-2-sulfonic acid sodium salt by a mixture of 2-amino-pyrimidine and sulfanilic acid, in the required stoichiometric proportions, 17.2 g. of the compound of formula (125) are obtained, corresponding to a yield of 86% of theory.

The compound (125) has the following elemental analysis by weight:

Analysis for $C_{13}H_9ClN_7NaO_3S$. 4.55 $H_2O$: Req. % C, 32.28; H, 3.77; N, 20.27; S, 6.63; Cl, 7.33; $H_2O$ 16.95 Found % C, 32.3; H, 3.8; N, 20.3; S, 6.5; Cl, 7.5; $H_2O$ 16.93.

EXAMPLE 26

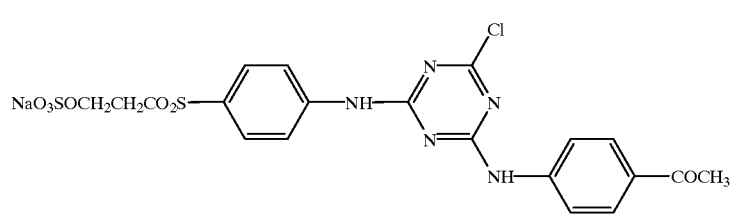

(126)

Using the procedure described in Example 8 but replacing 4 amino-stilbene-2-sulfonic acid sodium salt by a mixture of 2-(4-aminophenylsulfonyl)ethylhydrogen sulfate and 4-aminoacetophenone, in the required stoichiometric proportions, 8.9 g. of the compound of formula (126) are obtained, corresponding to a yield of 83% of theory.

The compound (126) has the following elemental analysis by weight:

Analysis for $C_{18}H_{17}ClN_5NaO_7S_2$. 3.38 $H_2O$: Req. % C, 36.10; H, 4.00; N, 11.70; S, 10.71; Cl, 5.92; $H_2O$ 10.17 Found % C, 37.0; H, 4.1; N, 11.8; S, 10.3; Cl, 5.8; $H_2O$ 10.18.

EXAMPLE 27

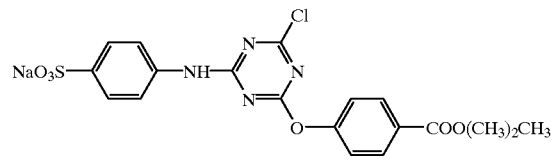
(127)

Using the procedure described in Example 8, compound (127) is prepared and has the following elemental analysis by weight:

Analysis for $C_{20}H_{18}ClNaO_6S$. 1.83 $H_2O$. 0.8 NaCl: Req. % C, 41.31; H, 3.78; N, 9.64; S, 5.51; Cl, 11.00; $H_2O$ 5.68 Found % C, 41.3; H, 3.7; N, 9.6; S, 5.3; Cl, 11.7; $H_2O$ 6.03.

EXAMPLE 28

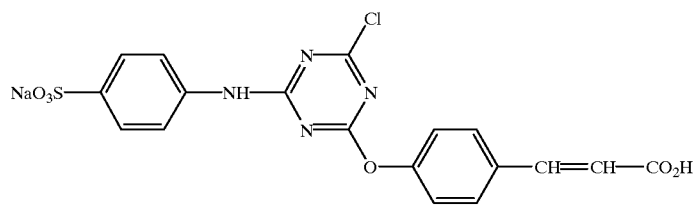
(128)

Using the procedure described in Example 8, compound (128) is prepared and has the following elemental analysis by weight:

Analysis for $C_8H_{12}ClNaO_6S$. 4 $H_2O$. 3.35 NaCl: Req. % C, 29.23; H, 2.71; N, 7.58; S, 4.33; Cl, 20.9; $H_2O$ 9.37 Found % C, 29.2; H, 2.7; N, 7.6; S, 4.3; Cl, 17.3; $H_2O$ 9.76.

EXAMPLE 29

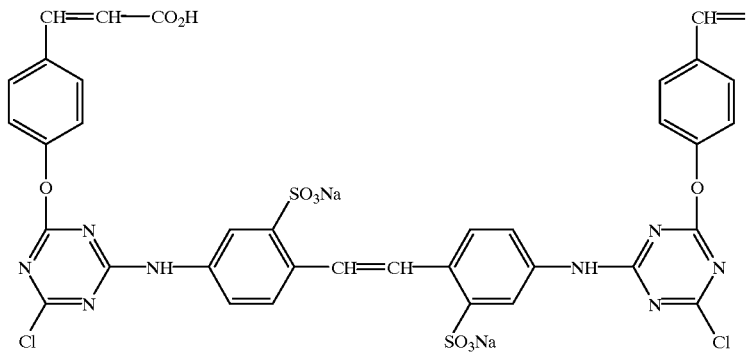
(129)

Using the procedure described in Example 18, compound (129) is prepared and has the following elemental analysis by weight:

Analysis for $C_{38}H_{24}Cl_2N_8Na_2O_{12}S_2$. 11.69 $H_2O$: Req. % C, 38.80; H, 4.06; N, 9.53; S, 5.45; Cl, 6.03; $H_2O$ 17.90 Found % C, 38.2; H, 4.0; N, 9.4; S, 5.3; Cl, 6.2; $H_2O$ 17.91.

EXAMPLE 30

(129)

[Chemical structure of compound 129: a symmetric bis-triazine stilbene compound with two OCH₃-phenyl-NH-triazine(Cl)-NH groups connected via a stilbene (CH=CH) bridge bearing two SO₃Na groups]

Using the procedure described in Example 18, compound (130) is prepared and has the following elemental analysis by weight:

Analysis for $C_{34}H_{26}Cl_2N_{10}Na_2O_8S_2$. 7.60 $H_2O$: Req. % C, 40.01; H, 4.07; N, 13.72; S, 6.28; Cl, 6.95; $H_2O$ 13.42 Found % C, 41.1; H, 3.8; N, 14.3; S, 5.8; Cl, 7.5; $H_2O$ 13.41.

EXAMPLES 31 TO 33

Separate samples of bleached cotton cretonne are foularded (80% liquor uptake) with an aqueous bath containing:

2 g/l 40% acetic acid 250 g/l product of Example 1, 3 or 4 to provide a concentration of 1% by weight of active ingredient on the cotton substrate.

As the product of Example 1, 3 or 4 is insoluble in water, it is added as a 5% (w/w) aqueous dispersion which is obtained by milling 5% of the product of Example 1, 3 or 4 and 1% of Pluronic F 108 (polypropylene glycol containing 80% ethylene oxide) in the presence of glass beads in deionised water.

The foularding is conducted at either alkaline pH (pH adjusted to 10–11 with soda) or at acidic pH (pH adjusted to 4–4.5 with acetic acid). Drying of the treated cotton samples is effected at 80° C. for two minutes, followed by thermofixing for one minute at 170° C.

The Sun Protection Factor (SPF) is determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

In order to evaluate the wash fastness of the treated cotton samples, respective samples are washed once, five times or ten times in an aqueous bath containing 7 g/l of a standard ECE detergent having the composition (weight %):

| | |
|---|---|
| 8.0% | Sodium alkylbenzene sulfonate |
| 2.9% | Tallow alcohol-tetradecane-ethylene glycol ether (14 mols EO) |
| 3.5% | Sodium soap |
| 43.8% | Sodium tripolyphosphate |
| 7.5% | Sodium silicate |

-continued

| | |
|---|---|
| 1.9% | Magnesium silicate |
| 1.2% | Carboxymethyl cellulose |
| 0.2% | EDTA |
| 21.2% | Sodium sulfate |
| | Water to 100%. |

Each wash is conducted at 60° C. for 15 minutes at a liquor ratio of 1:10.

The results obtained are set out in the following Table 1.

TABLE 1

| | | Treatment alkaline/ | SPF number of washes | | | |
|---|---|---|---|---|---|---|
| Example | Test UVA | acidic | none | one | five | ten |
| — | none (control) | acidic | 4.2 | | 4.2 | |
| 31 | cpd. of Ex. 1 | alkaline | 41 | 47 | 31 | 35 |
| 32 | cpd. of Ex. 4 | alkaline | 46 | 53 | 53 | 51 |
| | | acidic | 42 | 42 | 60 | 59 |
| 33 | cpd. of Ex. 3 | acidic | 38 | — | — | 44 |

EXAMPLE 34

Separate samples of bleached cotton cretonne are foularded (80% liquor uptake) with an aqueous bath containing:

2 g/l 40% acetic acid 12.5 g/l product of Example 2 to provide a concentration of 1% by weight of active ingredient on the cotton substrate.

As the product of Example 2 is insoluble in water, it is added as a 100% (w/w) aqueous dispersion which is obtained by milling 100% of the product of Example 2 and 1% of Pluronic F 108 in the presence of glass beads in deionised water.

The remaining procedure is as described in Examples 31 to 33.

The results obtained are set out in the following Table 2.

TABLE 2

| Example | Test UVA | Treatment alkaline/ acidic | SPF number of washes | | | |
|---|---|---|---|---|---|---|
| | | | none | one | five | ten |
| — | none (control) | acidic | 5.4 | 5.4 | 5.1 | 4.9 |
| 34 | cpd. of Ex. 2 | acidic | 30 | 38 | 34 | 37 |

EXAMPLE 35

Separate samples of bleached cotton cretonne are foularded (80% liquor uptake) with an aqueous bath containing:
15 g/l $MgCl_2$
250 g/l product of Example 5b
to provide a concentration of 1% by weight of active ingredient on the cotton substrate.

As the product of Example 5b is insoluble in water, it is added as a 5% (w/w) aqueous dispersion which is obtained by milling 5% of the product of Example 5b and 1% of Pluronic F 108 in the presence of glass beads in deionised water.

The remaining procedure is as described in Examples 31 to 33.

The results obtained are set out in the following Table 3.

TABLE 3

| Example | Test UVA | Treatment alkaline/ acidic | SPF number of washes | | | |
|---|---|---|---|---|---|---|
| | | | none | one | five | ten |
| — | none (control) | acidic | 5.4 | 5.4 | 5.1 | 4.9 |
| 35 | cpd. of Ex. 5b | Slightly acidic | 36 | 32 | 27 | 21 |

EXAMPLES 36 AND 37

Separate samples of bleached cotton cretonne are foularded (80% liquor uptake) with an aqueous bath containing:
5 g/l $NH_4Cl$
250 g/l product of Example 5b or 6
to provide a concentration of 1% by weight of active ingredient (product of Example 5b) or 0.2% by weight of active ingredient (product of Example 6), each based on the cotton substrate.

As the product of Example 5b or 6 is insoluble in water, it is added as a 5% (w/w) aqueous dispersion which is obtained by milling 5% of the product of Example 5b or 6 and 1% of Pluronic F 108 in the presence of glass beads in deionised water.

The remaining procedure is as described in Examples 31 to 33.

The results obtained are set out in the following Table 4.

TABLE 4

| Example | Test UVA | Treatment alkaline/ acidic | SPF number of washes | | | |
|---|---|---|---|---|---|---|
| | | | none | one | five | ten |
| — | none (control) | slightly acidic | 5.4 | 5.4 | 5.1 | 4.9 |
| 36 | cpd. of Ex. 5b | slightly acidic | 37 | 35 | 47 | 55 |
| 37 | cpd. of Ex. 6 | slightly acidic | 17 | 23 | 18 | 19 |

EXAMPLE 38

Separate samples of bleached cotton cretonne are foularded (80% liquor uptake) with an aqueous bath containing:
5 g/l $MgCl_2$
250 g/l product of Example 7
to provide a concentration of 0.1% or 0.5% by weight of active ingredient on the cotton substrate.

As the product of Example 7 is insoluble in water, it is added as a 5% (w/w) aqueous dispersion which is obtained by milling 5% of the product of Example 7 and 1% of Pluronic F 108 in the presence of glass beads in deionised water.

The remaining procedure is as described in Examples 31 to 33.

The results obtained are set out in the following Table 5.

TABLE 5

| Example | Test UVA | Concn. FWA | Treatment alkaline/ acidic | SPF number of washes | | | |
|---|---|---|---|---|---|---|---|
| | | | | none | one | five | ten |
| — | none (control) | — | acidic | 4.1 | 4.1 | 4.1 | 4.2 |
| 38 | cpd. of Ex. 7 | 0.1% | slightly acidic | 10 | 15 | 12 | 12 |
| | | 0.5% | acidic | 23 | 26 | 27 | 27 |

EXAMPLES 39 TO 51

Separate samples of bleached cotton cretonne are foularded (80% liquor uptake) with an aqueous bath containing:
10 g/l $Na_2SO_4$
50 g/i product of relevant Example
to provide a concentration of 0.1% or 0.2% by weight of active ingredient on the cotton substrate.

As the products of the relevant Examples are insoluble in water, they are added as a 5% (w/w) aqueous dispersion which is obtained by milling 5% of the product of the relevant Example and 1% of Pluronic F 108 in the presence of glass beads in deionised water.

The remaining procedure is as described in Examples 31 to 33.

The results obtained are set out in the following Table 6.

TABLE 6

| Example | Test UVA | Concn. FWA | Treatment alkaline/ acidic | SPF number of washes | | | |
|---|---|---|---|---|---|---|---|
| | | | | none | one | five | ten |
| — | none (control) | — | neutral | 7 | 5 | 5 | 6 |
| 39 | cpd. of Ex. 8 | 0.2% | neutral | 34 | 22 | 29 | 29 |
| 40 | cpd. of Ex. 10 | 0.1% | neutral | 29 | 31 | 22 | 19 |
| 41 | cpd. of Ex. 23 | 0.2% | neutral | 41 | 22 | 16 | 13 |
| 42 | cpd. of Ex. 11 | 0.1% | neutral | 39 | 36 | 22 | 23 |
| 43 | cpd. of Ex. 19 | 0.2% | neutral | 26 | 40 | 36 | 29 |
| 44 | cpd. of Ex. 21 | 0.1% | neutral | 21 | 19 | 13 | 11 |
| 45 | cpd. of Ex. 26 | 0.2% | neutral | 18 | 14 | 9 | 12 |
| 46 | cpd. of Ex. 29 | 0.2% | neutral | 30 | 34 | 31 | 28 |
| 47 | cpd. of Ex. 30 | 0.2% | neutral | 38 | 23 | 22 | 20 |
| 48 | cpd. of Ex. 17 | 0.2% | neutral | 18 | 13 | 7 | 15 |

TABLE 6-continued

| Example | Test UVA | Concn. FWA | Treatment alkaline/ acidic | SPF number of washes | | | |
|---|---|---|---|---|---|---|---|
| | | | | none | one | five | ten |
| 49 | cpd. of Ex. 18 | 0.2% | neutral | 29 | 36 | 21 | 19 |
| 50 | cpd. of Ex. 20 | 0.2% | neutral | 28 | 32 | 31 | 28 |
| 51 | cpd. of Ex. 22 | 0.2% | neutral | 20 | 13 | 8 | 7 |

EXAMPLES 52 TO 55

Separate samples of bleached cotton cretonne are foularded (80% liquor uptake) with an aqueous bath containing:

4 g/l NaHCO$_3$H 50 g/l urea 50 g/l product of relevant Example to provide a concentration of 0.2% by weight of active ingredient on the cotton substrate.

As the products of the relevant Examples are insoluble in water, they are added as a 5% (w/w) aqueous dispersion which is obtained by milling 5% of the product of the relevant Example and 1% of Pluronic F 108 in the presence of glass beads in deionised water.

The remaining procedure is as described in Examples 31 to 33 except that the thermofixing is conducted for 2 minutes at 130° C.

The results obtained are set out in the following Table 7.

TABLE 7

| Example | Test UVA | Concn. UVA | SPF number of washes | | | |
|---|---|---|---|---|---|---|
| | | | none | one | five | ten |
| — | none(control) | — | 7 | 5 | 5 | 4 |
| 52 | cpd. of Ex.17 | 0.2% | 28 | 15 | 15 | 24 |
| 53 | cpd. of Ex.18 | 0.2% | 45 | 49 | 45 | 34 |
| 54 | cpd. of Ex.20 | 0.2% | 33 | 35 | 36 | 48 |
| 55 | cpd. of Ex.6 | 0.2% | 29 | 27 | 26 | 21 |

The results in the Tables 1 to 7 demonstrate the substantial increase in the SPF values of cotton samples treated according to the present invention and that cotton samples treated according to the present invention are fast to washing.

We claim:

1. A method for the treatment of a textile fibre material, comprising treating the textile fibre material with 0.005 to 3.0% by weight, based in the weight of the textile fibre material, of one or more compounds of the formula:

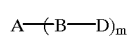
(1)

in which m is 1 or 2; A is a residue selected from those having the formulae:

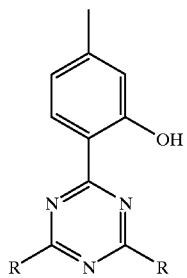
(2)

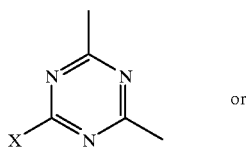
(3) or

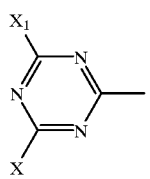
(4)

in which R is phenyl, optionally substituted by 1 or 2 $C_1$–$C_4$ alkyl groups, or by 1 or 2 $C_1$–$C_{18}$ alkoxy groups, or R is a group having the formula:

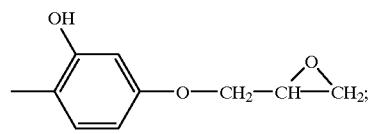

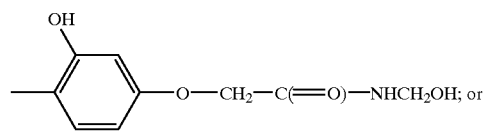

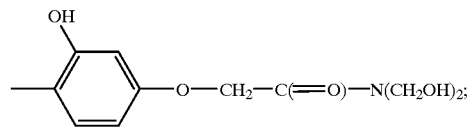

X is F, Cl or NHCH$_2$OH;

X$_1$ is F, Cl, NHCH$_2$OH or a group selected from those of the formulae:

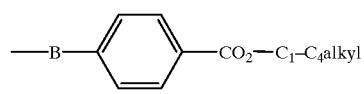

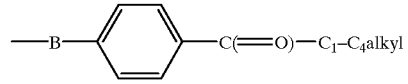

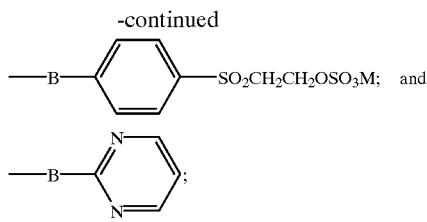

B is —O—, —NH— or —SO$_2$—; and

D is a group selected from those of the formulae:

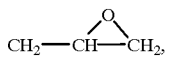

CH$_2$—C(=O)—NH(CH$_2$OH), CH$_2$—C(=O)—N(CH$_2$OH)$_2$ and CH$_2$CH$_2$—OSO$_3$M in which M is hydrogen, sodium, potassium, calcium, magnesium, ammonium, mono-, di-, tri- or tetra-C$_1$–C$_4$ alkylammonium, or ammonium that is di- or tri-substituted by a mixture of C$_1$–C$_4$ alkyl and C$_1$–C$_4$ hydroxy-alkyl groups or, when A is a residue of formula (5) or (6), D may also be a group selected from those having one of the formulae:

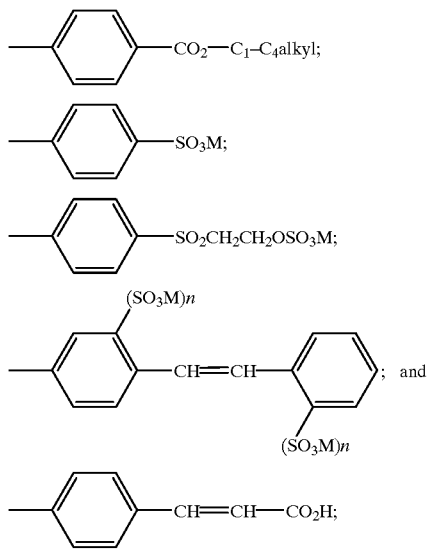

in which B and M have their previous significance and n is 0 or 1, provided that at least one SO$_3$M group is present, or D has the formula:

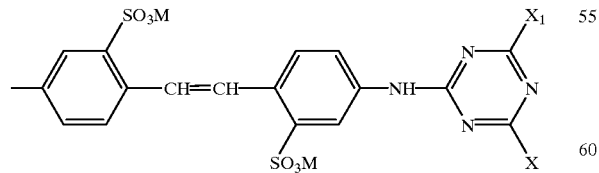

in which X, X$_1$ and M have their previous significance; provided that the following compounds are excluded:

a) those in which A is a residue of formula (2), (3) or (4), B is —O— and D is a group of formula

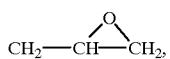

CH$_2$—C(=O)—NH(CH$_2$OH) or CH$_2$—C(=O)—N(CH$_2$OH)$_2$;

b) the compound 4-glycidyloxy-2-hydroxy-benzophenone; and c) the compound 2-(2-hydroxy-4-glycidyloxy)-4,6-(2,4-dimethylphenyl)-1,3,5-triazine.

2. A process according to claim 1 in which R is tolyl or xylyl.

3. A process according to claim 1 in which M is sodium.

4. A compound according to claim 1 in which the compound of formula (1) has the formula:

(7)

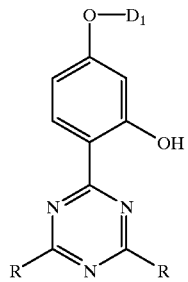

in which R is as defined in claim 2 and D$_1$ is a group having the formula

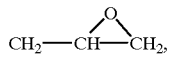

CH$_2$—C(=O)—NH(CH$_2$OH) or CH$_2$—C(=O)—N(CH$_2$OH)$_2$.

5. A process according to claim 1 in which the compound of formula (1) has the formula:

(10)

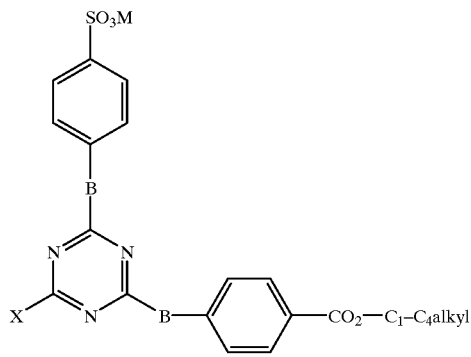

in which X is F or Cl and B and M are each as defined in claim 1.

6. A process according to claim 1 in which the compound of formula (1) has the formula:

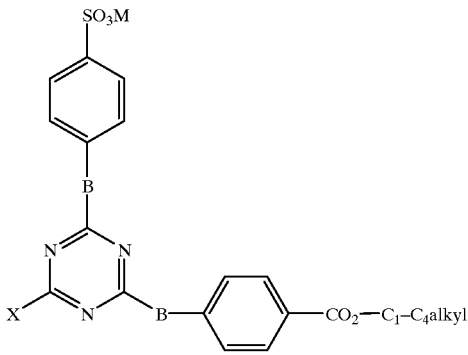

(11)

in which X is F or Cl and B and M are each as defined in claim 1.

7. A process according to claim 1 in which the compound of formula (1) has the formula:

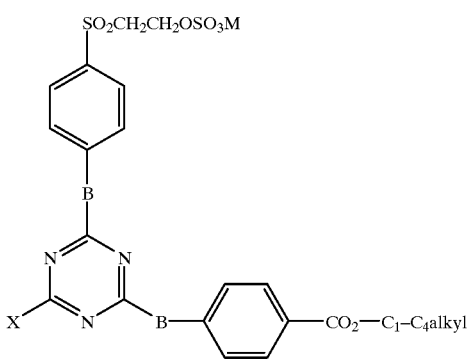

(12)

in which X is F or Cl and B and M are each as defined in claim 1.

8. A process according to claim 5 in which X is Cl, B is NH and M is Na.

9. A process according to claim 1 in which the compound of formula (1) has the formula:

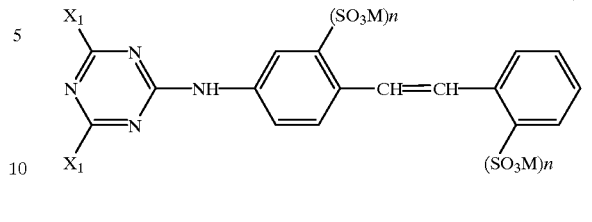

(13)

in which M and n are as defined in claim 1, provided that at least one $SO_3M$ group is present, X is F or Cl and $X_1$ is F, Cl or a group having one of the formulae:

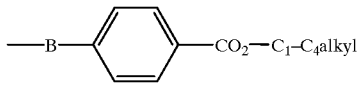

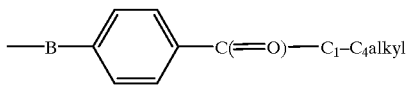

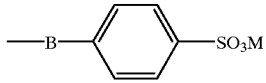

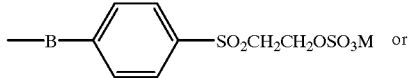 or

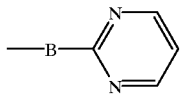

in which B and M are each as defined in claim 1.

10. A process according to claim 9 in which X is Cl, B is NH and M is Na.

11. A process according to claim 1 in which the compound of formula (1) has the formula:

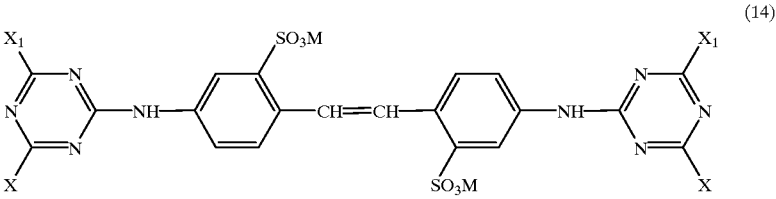

(14)

in which each X is the same and is F or Cl and each $X_1$ is the same and is F, Cl or a group having the formula:

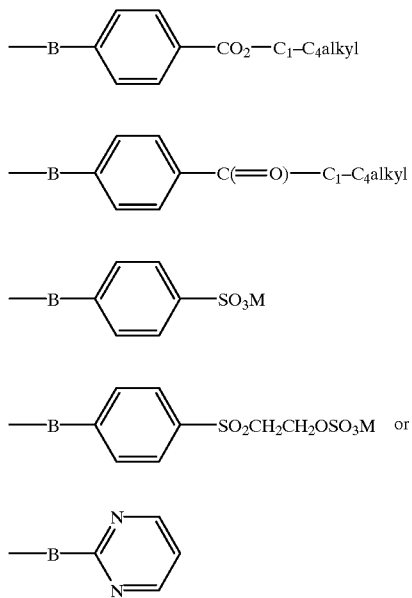

in which B and M are each as defined in claim 1.

12. A process according to claim 11 in which each X is Cl, B is NH and M is Na.

13. A process according to claim 1 in which the compound of formula (1) has the formula:

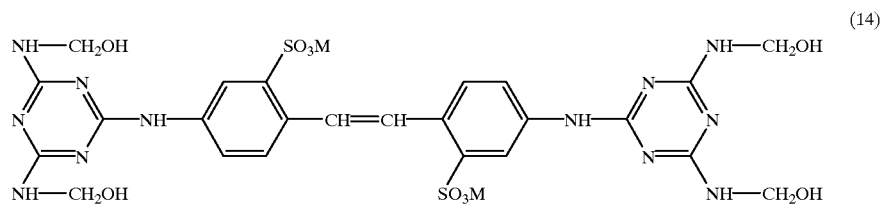

(14)

in which M is as defined in claim 1.

14. A process according to claim 13 in which M is Na.

15. A method according to claim 1 in which the textile fibres treated are cotton, viscose, flax, rayon, linen, wool, mohair, cashmere, angora, silk, polyester, polyamide or polyacrylonitrile fibres.

16. A method according to claim 15 in which the textile fibres treated are cotton fibres.

17. A method according to claim 1 in which the textile fibres treated have a density of less than 200 $g/m^2$ and have not been previously dyed in deep shades.

18. A method according to claim 1 in which the compound of formula (1) is only sparingly soluble in water and is applied in dispersed form.

19. A method according to claim 1 in which, in addition to the compound of formula (1), a minor proportion of one or more adjuvants is also employed.

20. A method according to claim 19 in which the adjuvants are emulsifiers, perfumes, colouring dyes, opacifiers, optical whitening agents, bactericides, nonionic surfactants, fabric care ingredients, anti-gelling agents or corrosion inhibitors.

21. A method according to claim 20 in which the amount of each of the adjuvants does not exceed 1% by weight on the treated fibre.

22. A method of increasing the SPF rating of textile fibre material, comprising treating the textile fibre material with 0.05 to 3.0% by weight, based on the weight of the textile fibre material, of one or more compounds having the formula (1) as defined in claim 1.

23. A method according to claim 22 whereby the tear resistance and/or lightfastness of the treated textile fibre material are also improved.

* * * * *